United States Patent [19]
Mougin et al.

[11] Patent Number: 5,945,095
[45] Date of Patent: Aug. 31, 1999

[54] COSMETIC COMPOSITION INCLUDING A POLYMERIC PARTICLE DISPERSION

[75] Inventors: Nathalie Mougin; Isabelle Bara, both of Paris; Jean Mondet, Aulnay-Sous-Bois, all of France

[73] Assignee: L'Oreal, Paris, France

[21] Appl. No.: 08/793,267

[22] PCT Filed: Jun. 17, 1996

[86] PCT No.: PCT/FR96/00930

§ 371 Date: Mar. 11, 1997

§ 102(e) Date: Mar. 11, 1997

[87] PCT Pub. No.: WO97/00662

PCT Pub. Date: Jan. 9, 1997

[30] Foreign Application Priority Data

Jun. 21, 1995 [FR] France ................... 95 07432
Jun. 21, 1995 [FR] France ................... 95 07430
Jun. 21, 1995 [FR] France ................... 95 07431
Jun. 21, 1995 [FR] France ................... 95 07429

[51] Int. Cl.$^6$ ........................................ A61K 7/48
[52] U.S. Cl. .................. 424/78.02; 424/47; 424/59; 424/61; 424/69; 424/70.1; 424/70.7; 424/78.08; 424/78.18; 424/450; 424/DIG. 5; 514/844; 514/845; 514/944
[58] Field of Search .............. 424/401, 47, 59, 424/61, 70.1, 70.7, 69, 78.02, 78.08, 78.18, 450, DIG. 5; 514/844, 845, 944

[56] References Cited

U.S. PATENT DOCUMENTS

| | | | |
|---|---|---|---|
| 4,996,044 | 2/1991 | Mercado et al. | 424/64 |
| 5,219,561 | 6/1993 | Gagnebien et al. | 424/69 |
| 5,223,559 | 6/1993 | Arraudeau et al. | 524/47 |
| 5,264,207 | 11/1993 | Bommelaer et al. | 424/69 |
| 5,643,581 | 7/1997 | Mougin et al. | 424/401 |

FOREIGN PATENT DOCUMENTS

| | | |
|---|---|---|
| 0195575 | 9/1986 | European Pat. Off. |
| 0409690 | 1/1991 | European Pat. Off. |
| 0447286 | 9/1991 | European Pat. Off. |
| 0486394 | 5/1992 | European Pat. Off. |
| 0497144 | 8/1992 | European Pat. Off. |
| 0502769 | 9/1992 | European Pat. Off. |
| 78094041 | 11/1978 | Japan . |
| 1202796 | 8/1970 | United Kingdom . |
| WO 95/09874 | 4/1995 | WIPO . |
| WO 97/00663 | 1/1997 | WIPO . |

*Primary Examiner*—Jyothsna Venkat
*Attorney, Agent, or Firm*—Finnegan, Henderson, Farabow, Garrett & Dunner, L.L.P.

[57] ABSTRACT

The present application relates to a composition, in particular a cosmetic, dermatological, hygiene or pharmaceutical composition, to care for and/or make up the skin, which composition may be in the form of a compact powder or a cast product, comprising a dispersion of polymer particles in a fatty substance. Furthermore, the invention relates to the use of this dispersion in such a composition.

47 Claims, No Drawings

COSMETIC COMPOSITION INCLUDING A POLYMERIC PARTICLE DISPERSION

The present invention relates to a cosmetic, dermatological, pharmaceutical or hygiene composition, in particular one to care for and/or make up the skin, which may be in the form of a cast product, a compact powder or any other form which is cosmetically acceptable, and comprising a dispersion of polymer particles in a liquid fatty substance, as well as to the use of such a dispersion in cosmetic compositions.

Cosmetic or dermatological compositions which may be applied to the skin or the lips as make-up or care product, such as lip bases, lipsticks or foundations, for example, generally contain fatty substances such as waxes, oils, pigments and/or fillers and, possibly, additives. It is known that the larger the amount of waxes present in the composition, the firmer is the consistency of this composition, thereby allowing its use in stick form. Compositions in the form of a flexible paste which can be applied using a brush, for example, are also known. These compositions generally contain a low amount of waxes, and fatty substances of pasty and/or oily type. The fatty substances of pasty type are generally present in large amounts, so as to obtain a composition whose consistency and viscosity are suitable for allowing it to be applied. However, it has been observed that these compositions have a certain capacity to migrate, that is to say a tendency to spread into the fine lines in the skin, in particular those around the lips, creating an aesthetically unpleasant effect, this migration being partly due to the presence of oily or pasty fatty substances. There is thus a need for a composition which migrates little after it has been applied to the skin and in the course of time.

The Applicant has observed, entirely surprisingly, that the use of a dispersion according to the invention in a cosmetic, dermatological, pharmaceutical or hygiene composition can allow a film of very good staying power to be obtained, which migrates little in the course of time, while at the same time being very pleasant to wear. This is particularly the case when the polymer in dispersion is a non-film-forming polymer, in particular one which is crosslinked.

Moreover, it has been observed that certain compositions according to the invention can conveniently soften the fine lines in the skin by camouflaging. Indeed, women, and even men, currently have a tendency to wish to appear young for as long as possible and consequently seek to soften the marks of ageing of the skin, which are reflected in particular by wrinkles and fine lines. It is common to combat the appearance of fine lines by treating the said wrinkles and fine lines with cosmetic products containing active agents which act on the skin, for example by moisturizing it or improving its cell renewal or alternatively by promoting the synthesis of collagen, of which the skin tissue is composed. Another possibility consists in masking or camouflaging fine lines which have already formed, for example using make-up products such as foundations or tinted creams.

However, the Applicant has observed, surprisingly and unexpectedly, that the use of a dispersion in a liquid fatty substance of surface-stabilized non-film-forming polymer particles, in a composition to be applied to the skin, can allow the "camouflaging" of wrinkles and fine lines which have already formed to be improved.

Without being bound by this explanation, it may be considered that when the composition is applied, the polymer particles in dispersion in the fatty substance will penetrate into the fine lines in the skin and thus camouflage them when the face is at rest. When the skin becomes deformed, for example during facial movements, the dispersion of polymer particles, which are not film-forming, will follow the movements of the face. The fatty substance of the dispersion, whose function is particularly to bind the particles together, as well as to bind them to the edges of the fine line, also referred to as the "lips" of the fine line, will ensure the adhesion and cohesion between the polymer particles and the lips of the fine line during facial movements, thereby also resulting in a certain level of softening of the said fine lines when the face is in movement.

It should be noted that the use of a dispersion in an oil of a fully film-forming polymer would not be suitable, given that the film obtained by coalescence of the particles could not become deformed, during facial movements, sufficiently easily and quickly to obtain the desired effect.

Moreover, the use of an aqueous dispersion of a non-film-forming polymer would also not be suitable. The reason for this is that, in this case, absorption of most of the water contained in the dispersion by the skin is observed. The result of this is that the polymer particles are no longer bound to each other and/or to the lips of the fine line, and therefore no longer make it possible to obtain the desired effect.

In the case of the dispersions according to the invention, it is possible for a small part of the fatty substance to be absorbed by the skin. However, the amount remaining in the dispersion is sufficient to allow good cohesion and adhesion, and thus adequate softening of the fine lines.

Moreover, the Applicant has observed, surprisingly and unexpectedly, that the use of a dispersion in an oil, of spherical surface-stabilized polymer particles, in a make-up composition for the eyes, can make it possible to lengthen and coat the eyelashes in a particularly noteworthy manner and to impart good remanence in water to the composition.

The aim of these compositions is to beautify the eyelashes by depositing a film thereon which can beautify, colour, lengthen and/or amplify them, while possibly protecting and/or treating them.

Lastly, the Applicant has observed, surprisingly and unexpectedly, that the use of a dispersion in an oil, of spherical surface-stabilized polymer particles, can make it possible to improve the compacting of compositions comprising a large amount of pulverulent compounds.

Indeed, compositions are known, in particular cosmetic, dermatological, pharmaceutical or hygiene compositions, which may be in the form of a so-called compact powder, obtained by compacting. These are generally anhydrous compositions which may consist mainly of solid particles and of a fatty binder, which are shaped by compression. Mention may be made in particular of eyeshadows and make-up rouges. However, the development of such compositions raises many difficulties since the final composition must be sufficiently homogeneous and compact to have a good capacity for being taken up and moreover to prevent fragmentation which may be caused in particular by impacts.

By means of the use of a composition according to the invention, a composition may be obtained in the form of a compact powder which is stable on storage and has good cohesion, thereby making it possible to avoid easy crumbling of the comnpacted product.

The subject of the invention is thus a cosmetic composition comprising fatty substances and pulverulent compounds, characterized in that it comprises a dispersion of surface-stabilized polymer particles in a liquid fatty substance. The subject of the invention is also a composition in the form of a cast product comprising at least one wax, characterized in that it also comprises a dispersion of crosslinked and surface-stabilized polymer particles in a cosmetically, dermatologically, hygienically or pharmaceutically acceptable liquid fatty substance.

The subject of the invention is also a composition in the form of a compact powder, comprising a fatty binder and pulverulent compounds, characterized in that it comprises a dispersion of surface-stabilized polymer particles in a cosmetically, dermatologically, pharmaceutically or hygienically acceptable liquid fatty substance.

The subject of the invention is also a composition comprising a dispersion of non-film-forming surface-stabilized polymer particles in a cosmetically, dermatologically, hygienically or pharmaceutically acceptable non-volatile liquid fatty substance, the said dispersion having a solids content of at least 15% by weight.

Another subject of the invention is the use, in a cosmetic composition for making up the eyes, comprising fatty substances and pulverulent compounds, of a dispersion of surface-stabilized polymer particles in a liquid fatty substance, in order to improve the lengthening of the eyelashes and/or to improve the remanence in water of the composition.

Another subject is the use, in a composition in the form of a cast product comprising at least one wax, of a dispersion of non-film-forming surface-stabilized polymer particles in a cosmetically, dermatologically, pharmaceutically or hygienically acceptable liquid fatty substance, for the purpose of attenuating the migration of the constituents of the composition into the fine lines in the skin and/or for the purpose of improving the staying power of the composition.

Another subject is the use, in a composition in the form of a compact powder comprising a fatty binder and pulverulent compounds, of a dispersion of surface-stabilized polymer particles in a cosmetically, dermatologically, pharmaceutically or hygienically acceptable liquid fatty substance, for the purpose of facilitating the compacting of the said composition.

Another subject is the use, in a cosmetic, dermatological, pharmaceutical or hygiene composition, of a dispersion of non-film-forming surface-stabilized polymer particles in a cosmetically, dermatologically, hygienically or pharmaceutically acceptable non-volatile liquid fatty substance, the said dispersion having a solids content of at least 15% by weight, for the purpose of softening the wrinkles and/or fine lines in the skin.

An advantage of the use of a particle dispersion according to the invention is that the particles remain in the form of elementary particles, without forming agglomerates, in the fatty substance, which would not be the case with inorganic particles of nanometric size.

Yet another advantage of such a dispersion is that it is possible to calibrate at will the size of the polymer particles and to modify their size polydispersity during the synthesis. It is thus possible to obtain very small particles, which are not visible to the eye when they are in the composition and when they are applied to the skin. This would not be possible with pigments in particulate form, since their constitution does not make it possible to modify the average size of the particles.

It has furthermore been observed that the compositions according to the invention to be spread on the skin and on semi-mucous or mucous membranes have particularly advantageous qualities of spreading and of adhesion to the skin, as well as a pleasant, creamy feel.

The compositions according to the invention thus comprise a stable dispersion of generally spherical particles of at least one surface-stabilized polymer in a cosmetically and/or dermatologically acceptable liquid fatty substance.

These dispersions may in particular be in the form of nanoparticles of polymers in stable dispersion in the said fatty substance. The nanoparticles are preferably of between 5 and 600 nm in size, given that beyond about 600 nm, the particle dispersions become much less stable.

The polymers used in the present application may be of any nature. It is thus possible to employ radical polymers, polycondensates or even polymers of natural origin. The polymer may be chosen by a person skilled in the art based on its properties, depending on the desired subsequent application for the composition.

Thus, the polymer may be film-forming or non-film-forming; in this second case, it may in particular be in the form of a crosslinked polymer.

It is thus possible to use film-forming polymers, preferably having a low glass transition temperature (Tg), which is less than or equal to room temperature. A dispersion is thus obtained which can form a film when it is applied onto a support, which is not the case when dispersions of inorganic pigments according to the prior art are used.

It is also possible to use non-film-forming polymers, which are optionally crosslinked, which may be used as fillers dispersed stably in an oil. The polymer used is crosslinked so as to prevent it from forming a film when it is applied to the skin. The crosslinking may be carried out by any means known to those skilled in the art. The crosslinking agent may be chosen from any crosslinking agent known in radical polymerization, in particular di- or multifunctional crosslinking agents such as ethylene glycol dimethacrylate or divinylbenzene.

The polymers which can be used in the context of the present invention preferably have a molecular weight of about from 2000 to 10,000,000, and a glass transition temperature of from $-100°$ C. to $300°$ C.

When the polymer has too high a Tg for the desired application, it may be combined with a plasticizer so as to lower the Tg of the mixture used. The plasticizer may be chosen from the plasticizers usually used in the field of application and, in particular, from compounds liable to be solvents for the polymer.

Among the non-crosslinked film-forming polymers which may be mentioned are vinyl or acrylic radical copolymers or homopolymers, preferably having a Tg of less than or equal to $30°$ C.

Among the non-film-forming polymers which may be mentioned are vinyl or acrylic radical copolymers or homopolymers, which are optionally crosslinked, preferably having a Tg of greater than or equal to $40°$ C., such as polymethyl methacrylate, polystyrene or poly-tert-butyl acrylate.

The liquid fatty substance in which the polymer particles are dispersed may consist of any cosmetically or dermatologically acceptable oil chosen, in particular, from carbon-based, hydrocarbon, fluoro and/or silicone oils of mineral, animal, plant or synthetic origin, alone or as a mixture, insofar as they form a homogeneous, stable mixture and insofar as they are compatible with the intended use.

The term liquid fatty substance is understood to refer to any non-aqueous medium which is liquid at room temperature.

Mention may thus be made of hydrocarbon oils such as liquid paraffin or liquid petrolatum; mink oil, turtle oil, soya oil, perhydrosqualene; sweet almond oil, calophyllum oil, palm oil, grapeseed oil, sesame oil, corn oil, rapeseed oil, sunflower oil, cotton oil, castor oil, avocado oil, jojoba oil, olive oil or cereal germ oil; esters of lanolic acid, of oleic acid, of lauric acid or of stearic acid; fatty esters such as isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl or diglyceryl triisostearate; higher fatty acids such as myristic acid, palmitic acid, stearic acid, behenic acid, oleic acid, linoleic acid, linolenic acid or isostearic acid; higher fatty alcohols such as cetanol, stearyl alcohol or oleyl alcohol, linoleyl or linolenyl alcohol, isostearyl alcohol or octyldodecanol; silicone oils such as PDMSs, which are optionally phenylated, such as phenyltrimethicones, or which are optionally substituted with aliphatic and/or aromatic groups, which are optionally fluorinated, or substituted with functional groups such as hydroxyl, thiol and/or amine groups; polysiloxanes modified with fatty acids, with fatty alcohols or with polyoxyalkylenes, fluoro silicones and perfluoro oils. Volatile oils such as cyclotetradimethylsiloxane, cyclopentadimethylsiloxane, cyclohexadimethylsiloxane and methylhexyldimethylsiloxane or isoparaffins such as "ISOPARs", in particular isododecane, may also be used.

In one specific embodiment of the invention, the liquid fatty substance is chosen from the group consisting of:
non-aqueous liquid compounds having a global solubility parameter according to the Hansen solubility space of less than 17 $(MPa)^{1/2}$,
or monoalcohols having a global solubility parameter according to the Hansen solubility space of less than or equal to 20 $(MPa)^{1/2}$,
or mixtures thereof.

The global solubility parameter δ, which is global according to the Hansen solubility space, is defined in the article "Solubility parameter values" by Eric A. Grulke in the publication "Polymer Handbook" 3rd Edition, chapter VII, pages 519–559, by the relationship:

$$\delta = (d_D^2 + d_P^2 + d_H^2)^{1/2}$$

in which
$d_D$ characterizes the London dispersion forces arising from the formation of dipoles induced during molecular impacts,
$d_P$ characterizes the Debye forces of interaction between permanent dipoles,
$d_H$ characterizes the specific forces of interaction (of the hydrogen bonding, acid/base, donor/acceptor, etc. type).

The definition of the solvents in the three-dimensional solubility space according to Hansen is described in the article by C. M. Hansen: "The three dimensional solubility parameters" J. Paint Technol. 39, 105 (1967).

Among the liquid fatty substances having a global solubility parameter according to the Hansen solubility space of less than or equal to 17 $(MPa)^{1/2}$ which may be mentioned are plant oils formed by fatty acid esters of polyols, in particular triglycerides, such as sunflower oil, sesame oil or rapeseed oil, or esters derived from acids or alcohols with a long chain (that is to say having from 6 to 20 carbon atoms), in particular esters or formula RCOOR' in which R represents a higher fatty acid residue containing from 7 to 19 carbon atoms and R' represents a hydrocarbon chain containing from 3 to 20 carbon atoms, such as palmitates, adipates and benzoates, in particular diisopropyl adipate. Mention may also be made of hydrocarbons and, in particular, liquid paraffin, liquid petrolatum, or hydrogenated polyisobutylene, isododecane or alternatively "ISOPARs", volatile isoparaffins. Mention may also be made of silicone oils such as polydimethylsiloxanes and polymethylphenylsiloxanes, which are optionally substituted with aliphatic and/or aromatic groups, which are optionally fluorinated, or with functional groups such as hydroxyl, thiol and/or amine groups, and volatile silicone oils, in particular cyclic ones. Mention may also be made of solvents, alone or as a mixture, chosen from (i) linear, branched or cyclic esters having more than 6 carbon atoms; (ii) ethers having more than 6 carbon atoms, (iii) ketones having more than 6 carbon atoms. The expression monoalcohols having a global solubility parameter according to the Hansen solubility space of less than or equal to 20 $(MPa)^{1/2}$ is understood to refer to aliphatic fatty alcohols having at least 6 carbon atoms, the hydrocarbon chain containing no substitution group. Monoalcohols according to the invention which may be mentioned are oleyl alcohol, decanol, dodecanol, octadecanol and linoleyl alcohol.

The choice of the non-aqueous medium is made by a person skilled in the art on the basis of the nature of the monomers constituting the polymer and/or the nature of the stabilizer, as indicated below.

In general, the dispersion according to the invention may be prepared in the following way, given by way of example.

The polymerization may be carried out in dispersion, that is to say by precipitation of the polymer which is being formed, with protection of the particles formed with a stabilizer. A mixture is thus prepared comprising the initial monomers as well as a radical initiator. This mixture is dissolved in a solvent which is referred to in the rest of the present description as the "synthesis solvent".

When the fatty substance is a non-volatile oil, the polymerization may be carried out in an apolar organic solvent (synthesis solvent), followed by addition of the non-volatile oil (which must be miscible with the said synthesis solvent) and selective distillation of the synthesis solvent.

A synthesis solvent is thus chosen such that the initial monomers and the radical initiator are soluble therein and the polymer particles obtained are insoluble therein, so that they precipitate therein when they are formed.

In particular, the synthesis solvent may be chosen from alkanes such as heptane or cyclohexane.

When the fatty substance chosen is a volatile oil, the polymerization may be carried out directly in the said oil which thus also acts as synthesis solvent. The monomers must also be soluble therein, as well as the radical initiator, and the polymer obtained must be insoluble therein.

The monomers are preferably present in the synthesis solvent, before polymerization, in a proportion of 5–20% by weight. The monomers may all be present in the solvent before the start of the reaction, or part of the monomers may be added as the polymerization reaction proceeds.

The radical initiator may in particular be azobisisobutyronitrile or 2-tert-butylperoxyethyl hexanoate.

The polymer particles are surface-stabilized, when they are formed during the polymerization, by means of a stabilizer which may be a sequential polymer, a grafted polymer and/or random polymer, alone or as a mixture.

The stabilization may be carried out by any known means, and in particular by adding the sequential polymer, grafted polymer and/or random polymer directly during the polymerization.

The stabilizer is preferably also present in the mixture before polymerization. However, it is also possible to add it continuously, in particular when the monomers are also added continuously.

2–30% by weight of stabilizer may be used relative to the initial monomer mixture, and preferably 5–20% by weight.

When a sequential and/or grafted polymer is used as stabilizer, the synthesis solvent is chosen such that at least part of the grafts or sequences of the said stabilizing polymer is soluble in the said solvent, the other part of the grafts or sequences not being soluble therein.

The insoluble part of the said stabilizing polymer then becomes adsorbed onto the surface of the polymer particles formed during the polymerization.

The stabilizing polymer used during the polymerization must be soluble, or dispersible, in the synthesis solvent and in the fatty substance.

Furthermore, a stabilizer whose insoluble grafts or sequences have a certain affinity for the polymer formed during the polymerization is preferably chosen. Among the grafted polymers which may be mentioned are silicone polymers grafted with a hydrocarbon chain; hydrocarbon polymers grafted with a silicone chain; grafted copolymers having, for example, an insoluble skeleton of polyacrylic type with soluble grafts of polyhydroxystearic acid type.

As sequential or grafted block copolymers comprising at least one block of polyorganosiloxane type and at least one block of a radical polymer, mention may be made of grafted copolymers of acrylic/silicone type which may be employed in particular when the non-aqueous medium contains silicone.

As sequential or grafted block copolymers comprising at least one block of polyorganosiloxane type and at least one polyether, dimethicone copolyols such as those sold under the name "Dow Corning 3225C" by the company Dow Corning and lauryl methicones such as those sold under the name "Dow Corning Q2-5200" by the company Dow Corning may be used.

As copolymers of acrylates or methacrylates of C1–C4 alcohols and of acrylates or methacrylates of C8–C30 alcohols, the stearyl methacrylate/methyl methacrylate copolymer may be used.

As sequential or grafted block copolymers comprising at least one block resulting from the polymerization of dienes, which is hydrogenated or non-hydrogenated, and at least one block of a vinyl polymer, mention may be made of sequential copolymers, in particular of "diblock" or "triblock" type of the polystyrene/polyisoprene, polystyrene/polybutadiene type such as those sold under the name "Luvitol HSB" by BASF, of the polystyrene/copoly(ethylene-propylene) type such as those sold under the name "Kraton" by Shell Chemical Co. or alternatively of the polystyrene/copoly (ethylene-butylene) type.

As sequential or grafted block copolymers comprising at least one block resulting from the polymerization of hydrogenated or non-hydrogenated dienes, and at least one block of an acrylic polymer, mention may be made of di- or trisequential poly(methyl methacrylate)/polyisobutylene copolymers or grafted copolymers containing a poly(methyl methacrylate) skeleton and containing polyisobutylene grafts.

As sequential or grafted block copolymers comprising at least one block resulting from the polymerization of hydrogenated or non-hydrogenated dienes and at least one block of a polyether, mention may be made of di- or trisequential polyoxyethylene/polybutadiene or polyoxyethylene/polyisobutylene copolymers.

When a random polymer is used as stabilizer, it is chosen such that it possesses a sufficient amount of groups which make it soluble in the intended synthesis solvent.

It is thus possible to employ copolymers of acrylates or methacrylates of C1–C4 alcohols and acrylates or methacrylates of C8–C30 alcohols. Mention may be made in particular of the stearyl methacrylate/methyl methacrylate copolymer.

When the synthesis solvent is apolar, it is preferable to choose as stabilizer a polymer which provides the most complete possible covering of the particles, several stabilizing polymer chains then being adsorbed onto a polymer particle obtained by polymerization.

In this case, it is preferred to use as stabilizer either a grafted polymer or a sequential polymer, so as to have better interface activity. The reason for this is that the sequences or grafts which are insoluble in the synthesis solvent provide more voluminous covering to the surface of the particles.

Moreover, when the liquid fatty substance comprises at least one silicone oil, the stabilizer is preferably chosen from the group consisting of sequential or grafted block copolymers comprising at least one block of polyorganosiloxane type and at least one block of a radical polymer or of a polyether or of a polyester. When the liquid fatty substance does not comprise a silicone oil, the stabilizer is preferably chosen from the group consisting of:

(a) sequential or grafted block copolymers comprising at least one block of polyorganosiloxane type and at least one block of a radical polymer or of a polyether or of a polyester, (b) copolymers of acrylates or methacrylates of $C_1$–$C_4$ alcohols and acrylates or methacrylates of $C_8$–$C_{30}$ alcohols, (c) sequential or grafted block copolymers comprising at least one block resulting from the polymerization of hydrogenated or non-hydrogenated dienes, and at least one block of a vinyl or acrylic polymer or of a polyether or of a polyester, or mixtures thereof.

The dispersions obtained according to the invention may then be used in a composition, in particular a cosmetic, pharmaceutical and/or hygiene composition, such as a composition to care for or make up the skin or keratin substances, or alternatively a hair composition or a sun composition.

Depending on the application, it may be chosen to use film-forming or non-film-forming polymer dispersions, in volatile or non-volatile oils.

The composition according to the invention may comprise, depending on the type of application envisaged, the constituents conventionally used in the fields considered, which are present in an amount which is is suitable for the desired pharmaceutical form.

In particular, the composition may comprise pulverulent compounds and/or, besides the liquid fatty substance of the dispersion, additional fatty substances which may be chosen from waxes, oils, gums and/or pasty fatty substances, which are of plant, animal, mineral or synthetic origin, or even silicone-based.

However, it is possible not to add other fatty substances, in particular when the oil used for the particle dispersion is in sufficient amount within the context of the application envisaged.

Among the waxes which may be present in the composition according to the invention, mention may be made of hydrocarbon waxes such as beeswax; carnauba wax, candelilla wax, ouricurry wax, Japan wax, cork fibre wax or sugar cane wax; paraffin wax, lignite wax; microcrystalline waxes; lanolin wax; montan wax; ozokerites; polyethylene waxes; the waxes obtained by Fischer-Tropsch synthesis; hydrogenated oils, fatty esters and glycerides which are solid at 25° C. It is also possible to use silicone waxes, among which mention may be made of polymethylsiloxane alkyls, alkoxys and/or esters. The waxes may be in the form of stable dispersions of colloidal wax particles such that they may be prepared according to known methods, such as "Microemulsions Theory and Practice", L. M. Prince Ed., Academic Press (1977), pages 21–32.

The waxes may be present in a proportion of 5–50% by weight in the composition, in particular when the said composition finds an application as a mascara.

Among the oils which may be present in the composition according to the invention, mention may be made of hydrocarbon oils such as liquid paraffin or liquid petrolatum; perhydrosqualene; arara oil; sweet almond oil, calophyllum oil, palm oil, castor oil, avocado oil, jojoba oil, olive oil or cereal germ oil; esters of lanolic acid, of oleic acid, of lauric acid or of stearic acid; alcohols such as oleyl alcohol, linoleyl alcohol or linolenyl alcohol, isostearyl alcohol or octyldodecanol. Mention may also be made of silicone oils such as PDMSs, which are optionally phenylated, such as phenyltrimethicones. It is also possible to use volatile oils such as cyclotetradimethylsiloxane, cyclopentadimethylsiloxane, cyclohexadimethylsiloxane, methylhexyldimethylsiloxane or isoparaffins.

In particular, in order to facilitate the application of the composition, volatile fatty substances may be introduced therein.

When the composition according to the invention finds an application as a compacted powder, the fatty phase, usually referred to as the binder, may preferably be present in the composition in a proportion of 2–20% by weight.

The composition may also comprise pulverulent compounds, for example in a proportion of 0–98% by weight, which may be chosen from pigments and/or pearlescent agents and/or fillers usually used in cosmetic compositions. The pigments may be white or coloured and inorganic and/or organic. Among the inorganic pigments which may be mentioned are titanium dioxide, which is optionally surface-treated, zirconium oxide or cerium oxide, as well as iron oxide or chromium oxide, manganese violet, ultramarine blue, chromium hydrate and ferric blue.

Among the organic pigments which may be mentioned are carbon black, pigments of D&C type and lakes based on cochineal carmine, barium, strontium, calcium and aluminium.

The pearlescent pigments may be chosen from white pearlescent pigments such as mica coated with titanium, or with bismuth oxychloride, coloured pearlescent pigments such as titanium mica with iron oxides, titanium mica with, in particular, ferric blue or chromium oxide, titanium mica with an organic pigment of the abovementioned type and pearlescent pigments based on bismuth oxychloride.

The fillers may be inorganic or organic and lamellar or spherical. Mention may be made of talc, mica, silica, kaolin, nylon powder, poly-β-alanine powder and polyethylene powder, Teflon, lauroyllysine, starch, boron nitride, tetrafluoroethylene polymer powders, hollow microspheres such as Expancel (Nobel is Industrie), polytrap (Dow Corning) and silicone resin microbeads (Tospearls from Toshiba for example), precipitated calcium carbonate, magnesium carbonate and hydrocarbonate, hydroxyapatite, hollow silica microspheres (Silica Beads from Maprecos), glass or ceramic microcapsules; metal soaps derived from organic carboxylic acids having from 8 to 22 carbon atoms, preferably from 12 to 18 carbon atoms, for example zinc, magnesium or lithium stearate, zinc laurate and magnesium myristate.

The composition may also comprise any additive usually used in such compositions, such as thickeners, antioxidants, fragrances, preserving agents, cosmetic active agents, moisturizers, vitamins, essential fatty acids, sphingo lipids, sunscreens, surfactants, liposoluble polymers such as polyalkylenes, in particular polybutene, polyacrylates and silicone polymers which are compatible with fatty substances. Obviously, a person skilled in the art will take care to select this or these possible additional compounds, and/or the amount thereof, such that the advantageous properties of the composition according to the invention are not, or are substantially not, adversely affected by the addition envisaged.

When the application envisaged for the composition is an application as a mascara, the composition according to the present invention may in particular be in the form of a suspension, a solution or a microdispersion of waxes in a solvent medium, in anhydrous solid or pasty form, or alternatively in the form of an oily gel. Indeed, it has been observed that the use of a composition according to the invention, comprising fatty substances and pulverulent compounds, and a dispersion of surface-stabilized polymer particles in a fatty substance, makes it possible to obtain adequate coating of the eyelash, which is reflected by a consequent lengthening of the said eyelash, and good remanence in water of the composition.

In another embodiment of the invention, the compositions according to the invention may be in the form of a cast product and comprise at least one wax, and a dispersion of crosslinked and surface-stabilized polymer particles in a cosmetically, dermatologically, hygienically or pharmaceutically acceptable liquid fatty substance. The compositions may then be in the form of a stick or pencil, or in the form of a flexible paste, with a dynamic viscosity at 25° C. of about 3–30 Pa·s. They may be in the form of a cast product, prepared in a manner which is common to those skilled in the art, or alternatively in the form of a cupel which can be used by direct contact or with a sponge. in particular, they find an application as cast foundation, cast make-up rouge or eyeshadow, lipstick or a care base for the lips, or a care balm.

When it is in the form of a powder, in particular a compacted powder, the composition according to the invention may be prepared by a person skilled in the art in the usual manner, and in particular by mixing the various constituents and compacting using a mechanical press. The composition thus obtained therefore has the appearance of a compacted powder, for example in cupel, stick or cylinder form or in any other complex form. The composition according to the invention may be in the form of a pharmaceutical or hygiene composition such as a body powder, a baby powder or an antiperspirant powder. It may also be in the form of a make-up product such as a make-up rouge or an eyeshadow, a blusher or a face powder.

The compositions of the invention may also in particular be in the form of oily gel, oily liquid or oil, paste, stick or aerosol or alternatively in the form of a vesicle dispersion containing ionic and/or nonionic lipids. These pharmaceutical forms are prepared according to the usual methods of the fields considered. These compositions for topical application may in particular constitute a cosmetic, dermatological, hygiene or pharmaceutical composition for protection, treatment or care of the face, the neck, the hands or the body (for example an anhydrous care cream, a sun oil or a body gel), a make-up composition (for example a make-up gel) or an artificial tanning composition.

The invention is illustrated in greater detail in the examples which follow.

Examples 1 to 6 describe the preparation of several dispersions of polymer particles in an oil.

Examples 7 to 12 describe make-up compositions comprising a dispersion according to the invention.

EXAMPLE 1

360 g of n-heptane and 15 g of sequential stabilizing polymer of polystyrene/copoly(ethylenepropylene)diblock copolymer type sold under the name Kraton G1701 (Shell) are mixed together.

The mixture is heated for at least 3 h, at about 60° C., in order to obtain a dispersed solution.

At 25° C., 19 g of methyl methacrylate, 1 g of ethylene glycol dimethacrylate, 0.4 g of 2-tert-butylperoxyethyl hexanoate (Trigonox 21S from Akzo) and 5 g of heptane are added to the mixture.

The mixture is heated at 75° C., under nitrogen, for at least 3 hours.

A mixture of 76 g of methyl methacrylate, 4 g of ethylene glycol dimethacrylate, 1.6 g of 2-tert-butylperoxyethyl hexanoate (Trigonox 21S from Akzo) and 80 g of heptane are then added, at 75° C. and over 1.5 hours.

At the end of the addition, the mixture is heated at 85° C. for 4 hours, 1 g of Trigonox dissolved in 5 g of heptane is added and the mixture is heated for a further 7 hours at 85° C.

A stable dispersion of milky appearance is obtained, with a solids content of 18.6% by weight.

Measurement of the particle size, made by quasi-elastic light scattering with a Coulter N4 SD machine, gives the following results:

average particle size: 160 nm polydispersity: less than 0.1.

50 g of the above dispersion in heptane are mixed with 28.5 g of non-volatile liquid paraffin. The heptane is selectively evaporated off using a rotary evaporator.

A stable dispersion of milky appearance is then obtained, having a solids content of 25% by weight, of polymethyl methacrylate crosslinked with ethylene glycol dimethacrylate, in a liquid paraffin.

EXAMPLE 2

A dispersion of polymethyl methacrylate crosslinked with ethylene glycol dimethacrylate, in a branched and volatile liquid paraffin (Isopar L from Exxon) which is a C-10 to C-12 isoalkane, is prepared according to the method of Example 1, replacing the heptane by the said liquid paraffin Isopar L.

A stable dispersion is thus obtained, having a solids content of 19% by weight and an average particle size of 159 nm (polydispersity: 0.05).

EXAMPLE 3

20 g of the above dispersion in Isopar are mixed with 16.2 g of cyclotetradimethylsiloxane (volatile silicone oil).

A stable dispersion of milky appearance is then obtained, consisting of 3.8 g of polymethyl methacrylate crosslinked with ethylene glycol dimethacrylate, 16.2 g of volatile liquid paraffin and 16.2 g of volatile silicone oil.

EXAMPLE 4

20 g of the dispersion in Isopar of Example 2 are mixed with 16.2 g of $C_{12}$–$C_{15}$ alkyl benzoate (Finsolv TN from Witco).

A stable dispersion of milky appearance is then obtained, consisting of 3.8 g of polymethyl methacrylate crosslinked with ethylene glycol dimethacrylate, 16.2 g of volatile liquid paraffin and 16.2 g of non-volatile ester.

EXAMPLE 5

360 g of n-heptane and 15 g of sequential stabilizing polymer of polystyrene/copoly(ethylenepropylene)diblock copolymer type sold under the name Kraton G1701 (Shell) are mixed together.

The mixture is heated for at least 3 h, at about 60° C., in order to obtain a dispersed solution.

At 25° C., 20 g of methyl acrylate, 0.4 g of 2-tert-butylperoxyethyl hexanoate and 5 g of heptane are added to the mixture.

The mixture is heated at 75° C., under nitrogen, for 3 hours. A mixture of 80 g of methyl acrylate, 1.6 g of 2-tert-butylperoxyethyl hexanoate and 80 g of heptane are added, at 75° C. and over 1.5 hours.

At the end of the addition, the mixture is heated at 85° C. for 4 hours, 1 g of Trigonox dissolved in 5 g of heptane is then added and the mixture is heated for a further 7 hours at 85° C.

A stable dispersion of milky appearance is obtained, with a solids content of 19% by weight.

Measurement of the particle size, made by quasi-elastic light scattering with a Coulter N4 SD machine, gives the following results:

average particle size: 230 nm polydispersity: less than 0.1.

50 g of she above dispersion in heptane are mixed with 28.5 g of non-volatile liquid paraffin. The heptane is selectively evaporated off using a rotary evaporator.

A stable dispersion of milky appearance is then obtained, having a solids content of 25% by weight, of polymethyl acrylate (Tg=10° C.) in a non-volatile liquid paraffin.

EXAMPLE 6

A dispersion of polymethyl acrylate in a branched and volatile liquid paraffin (Isopar L from Exxon) is prepared in the same way as in Example 5, replacing the heptane by the said liquid paraffin Isopar L.

A stable dispersion is thus obtained, having a solids content of 20% by weight and an average particle size of 197 nm (polydispersity: 0.06).

This dispersion is film-forming and gives, after drying, a continuous and transparent film.

EXAMPLE 7

Waterproof Mascara

The composition is prepared in the following way: the components of phase A are melted, the pigments are added thereto and mixing is carried out. The components of phase B are mixed together and are added to the components of phase A.

| Phase A | |
|---|---|
| paraffin wax | 12 g |
| lanolin alcohol | 15 g |
| black iron oxide | 5 g |
| Phase B | |
| montmorillonite | 8 g |
| starch | 2 g |
| isoparaffin | 45 g |
| dispersion according to Example 1 | 5 g |

A mascara having good cosmetic properties is obtained.

EXAMPLE 8

A lipstick is prepared in the form of a soft paste having the following composition:

| | |
|---|---|
| waxes (beeswax and carnauba) | 5 g |
| oils | 20 g |
| acetylated lanolin | 20 g |
| lanolin | 30 g |
| fillers | 10 g |
| pigments | 10 g |
| dispersion according to Example 1 | 5 g |

The composition is prepared by heating the various ingredients to 95–100° C., while mixing so as to obtain a perfectly homogeneous mixture.

After cooling, a lipstick which is easy to apply and which allows a film which is pleasant to wear to be produced is obtained.

It is observed that the film does not migrate into the fine lines in the skin, even after it has been worn for several hours.

EXAMPLE 9

A lipstick is prepared in the form of a stick having the following composition:

| | |
|---|---|
| castor oil | 15 g |
| jojoba oil | 13 g |
| hydrogenated coconut oil | 7 g |
| isopropyl lanolate | 25 g |
| carnauba wax | 10 g |
| polyethylene wax | 10 g |
| pigments and fillers | 15 g |
| dispersion of Example 1 | 5 g |

The stick is prepared in the following way: the fatty phase is heated to a temperature of about 100° C., the fillers and pigments are added and everything is then mixed together using a Moritz turbomixer at a speed of 3000 rev/min. The said mixture can then be cast into suitable moulds.

The composition obtained is easy and pleasant to apply. It is observed that the film does not migrate into the fine lines in the skin, even after it has been worn for several hours.

EXAMPLE 10

A compacted powder having the following composition is prepared:

| | |
|---|---|
| Composition A | |
| Talc | 30 g |
| Bismuth oxychloride | 10 g |
| Zinc stearate | 4 g |
| Nylon powder | 20 g |
| Dispersion of Example 5 | 5 g |
| Composition B | |
| Iron oxides | 2 g |
| Liquid petrolatum | 6 g |

The powder is obtained in the following way: composition A is ground in a mill of Kenwood type for about 5 minutes with gentle stirring, composition B is added and the mixture is ground for about 2 minutes at the same speed, then for 3 minutes at a faster speed. The preparation is then screened through a 0.16-mm screen and this mixture is then compacted in cupels.

A compacted powder having good adhesion is obtained, which spreads well and pleasantly on the skin, while feeling soft to the touch.

EXAMPLE 11

Facial Gel

The following composition is prepared:

| | |
|---|---|
| Isopropyl palmitate | 10 g |
| Petrolatum (wax) | 5 g |
| Modified hectorite (clay) | 0.15 g |
| Ozokerite (wax) | 5 g |
| Oxyethylenated sorbitan septaoleate (40 EO) | 5 g |
| Dispersion of Example 1 (25% solids content) | 75 g |

A gel having good cosmetic properties is obtained.

EXAMPLE 12

Care Oil

The following composition is prepared:

| | |
|---|---|
| Dispersion of Example 2 (25% solids content) | 70 g |
| Jojoba oil | 15 g |
| Soya oil | 15 g |

A care oil which may be applied to the body or the face is obtained.

We claim:

1. A cosmetic composition comprising:
   at least one fatty substance and optionally at least one pulverulent compound, and
   a non-aqueous dispersion of surface-stabilized polymer particles in at least one liquid fatty substance, wherein said particles are particles of at least one polymer, and wherein said polymer particles are stabilized by at least one surface-stabilizing polymer.

2. A composition in the form of a cast product comprising:
   at least one wax, and
   a non-aqueous dispersion of crosslinked and surface-stabilized polymer particles in a cosmetically, dermatologically, hygienically or pharmaceutically acceptable liquid fatty substance, wherein said polymer particles are stabilized by at least one surface-stabilizing polymer.

3. A composition in the form of a compact powder comprising:
   at least one fatty binder and at least one pulverulent compound, and
   a non-aqueous dispersion of surface-stabilized polymer particles in a cosmetically, dermatologically, pharmaceutically or hygienically acceptable liquid fatty substance, wherein the particles are stabilized by at least one surface-stabilizing polymer.

4. A composition comprising a non-aqueous dispersion of non-film-forming surface-stabilized polymer particles in a cosmetically, dermatologically, hygienically or pharmaceutically acceptable non-volatile liquid fatty substance, wherein said dispersion has a solids content of at least 15% by weight, and wherein the particles are stabilized by at least one surface-stabilizing polymer.

5. A composition according to claim 1, wherein said at least one polymer is a radical polymer, a polycondensate, or a polymer of natural origin.

6. A composition according to claim 1, wherein said at least one liquid fatty substance comprises at least one oil which is a carbon-based oil of mineral, animal, plant or synthetic origin, a hydrocarbon oil of mineral, animal, plant or synthetic origin, a fluoro oil of mineral, animal, plant or synthetic origin, or a silicone oil of mineral, animal, plant or synthetic origin.

7. A composition according to claim 1, wherein said at least one liquid fatty substance is a liquid paraffin, a liquid petrolatum, a mink oil, a turtle oil, a soya oil, a perhydrosqualene, a sweet almond oil, a calophyllum oil, a palm oil, a grapeseed oil, a sesame oil, a corn oil, a grapeseed oil, a sunflower oil, a cotton oil, a castor oil, an avocado oil, a jojoba oil, an olive oil, a cereal germ oil, an ester of lanolic acid, an ester of oleic acid, an ester of lauric acid, an ester of stearic acid, a fatty ester, a higher fatty acid, a higher fatty alcohol, a silicone oil, which is optionally phenylated or which is optionally substituted with an aliphatic group or an aromatic group, wherein said aliphatic group or said aromatic group is optionally fluorinated, or substituted with functional groups; a polysiloxane modified with fatty acids, with fatty alcohols or with polyoxyalkylenes, a fluoro silicone, a perfluoro oil, an isoparaffin, or a volatile oil.

8. A composition according to claim 7, wherein said fatty ester is an isopropyl myristate, an isopropyl palmitate, a butyl stearate, a hexyl laurate, a diisopropyl adipate, an isononyl isononate, a 2-ethylhexyl palmitate, a 2-hexyldecyl laurate, a 2-octyldecyl palmitate, a 2-octyldodecyl myristate, a 2-octyldodecyl lactate, a 2-diethylhexyl succinate, a diisostearyl malate, a glyceryl or a diglyceryl triisostearate.

9. A composition according to claim 7, wherein said higher fatty acid is a myristic acid, a palmitic acid, a stearic acid, a behenic acid, an oleic acid, a linoleic acid, a linolenic acid or an isostearic acid.

10. A composition according to claim 7, wherein said higher fatty alcohol is a cetanol, a stearyl alcohol, an oleyl alcohol, a linoleyl alcohol, a linolenyl alcohol, an isostearyl alcohol, or an octyldodecanol.

11. A composition according to claim 7, wherein said silicone oil is a polydimethylsiloxane.

12. A composition according to claim 7, wherein said optionally phenylated silicone is a phenyltrimethicone.

13. A composition according to claim 7, wherein said substituted functional groups on said silicone oil are hydroxyl, thiol or amine groups.

14. A composition according to claim 7, wherein said volatile oil is a cyclotetradimethylsiloxane, a cyclopentadimethylsiloxane, a cyclohexadimethylsiloxane, or a methylhexyldimethyl-siloxane.

15. A composition according to claim 7, wherein said isoparaffin is a C-10 to C-12 isoalkane.

16. A composition according to claim 15, wherein said C-10 to C-12 isoalkane is isododecane.

17. A composition according to claim 1, wherein said at least one liquid fatty substance is:
a non-aqueous liquid compound having a global solubility parameter according to the Hansen solubility space of less than 17 $(MPa)^{1/2}$, or
a monoalcohol having a global solubility parameter according to the Hansen solubility space of less than or equal to 20 $(MPa)^{1/2}$.

18. A composition according to claim 1, wherein said at least one surface-stabilizing polymer is a sequential polymer, a grafted polymer or a random polymer.

19. A composition according to claim 18, wherein said at least one surface-stabilizing polymer is a silicone polymer grafted with a hydrocarbon chain; a hydrocarbon polymer grafted with a silicone chain; a grafted copolymer having an insoluble skeleton of polyacrylic structure with soluble grafts of polyhydroxystearic acid; a sequential or grafted block copolymer comprising at least one block of polyorganosiloxane structure and at least one block of a radical polymer; a sequential or grafted block copolymer comprising at least one block of polyorganosiloxane structure and at least one polyether; a copolymer of acrylates or methacrylates of $C_1$–$C_4$ alcohols or of acrylates or methacrylates of $C_8$–$C_{30}$ alcohols; a sequential or grafted block copolymer comprising at least one block resulting from the polymerization of dienes and at least one block of a vinyl polymer; a sequential or grafted block copolymer comprising at least one block resulting from the polymerization of dienes and at least one block of an acrylic polymer; or a sequential or grafted block copolymer comprising at least one block resulting from the polymerization of dienes and at least one block of a polyether.

20. A composition according to claim 1, wherein said at least one fatty substance is a wax which is of plant, animal, mineral or synthetic origin or which is silicone-based, an oil which is of plant, animal, mineral or synthetic origin or which is silicone-based, a gum which is of plant, animal, mineral or synthetic origin or which is silicone-based, or a pasty fatty substance which is of plant, animal, mineral or synthetic origin or which is silicone-based.

21. A composition according to claim 1, wherein said composition is in the form of a suspension, a solution or a microdispersion of waxes in a solvent medium; in anhydrous solid or pasty form; or in the form of an oily gel.

22. A composition according to claim 21, wherein said composition is in the form of a mascara.

23. A composition according to claim 1, wherein said composition is in the form of a stick or pencil; in the form of a flexible paste, with a dynamic viscosity at 25° C. of about 3–30 Pa·s; or in the form of a cupel.

24. A composition according to claim 1, wherein said composition is a skin care product or a make-up product.

25. A composition according to claim 24, wherein said composition is in the form of a cast foundation, a cast make-up rouge or eyeshadow, a lipstick or a care base for the lips, or a care balm.

26. A composition according to claim 1, wherein said composition is in the form of a body powder, a baby powder, an antiperspirant powder or a make-up product.

27. A composition according to claim 26, wherein said make-up product is a make-up rouge or eyeshadow, a blusher or a face powder.

28. A composition according to claim 1, wherein said composition is in the form of an oily gel, an oily liquid, an oil, a paste, a stick, an aerosol, or a vesicle dispersion containing at least one lipid which is ionic or nonionic.

29. A composition according to claim 1, wherein said composition is in the form of an antisun composition, an artificial tanning composition, or a cosmetic, dermatological, hygiene or pharmaceutical composition for protection, treatment or care of the face, the neck, the hands or the body.

30. A method for improving the lengthening of the eyelashes for improving the remanence in water of a cosmetic composition for making up the eyes, said method comprising applying to the eyes a cosmetic composition comprising at least one fatty substance and/or at least one pulverulent compound and a non-aqueous dispersion of surface-stabilized polymer particles in at least one liquid fatty substance, wherein the particles are stabilized by at least one surface-stabilizing polymer.

31. A method for attenuating the migration of the constituents of a cosmetic composition into the fine lines in the skin for improving the staying power of a cosmetic composition on the skin, said method comprising applying to the skin a composition in the form of a cast product containing at least one wax and a non-aqueous dispersion of non-filmforming surface-stabilized polymer particles in at least one cosmetically, dermatologically, pharmaceutically or hygienically acceptable liquid fatty substance, wherein the particles are stabilized by at least one surface-stabilizing polymer.

32. A method for facilitating the compacting of a cosmetic composition in the form of a compact powder, said method comprising preparing a composition in the form of a compact powder containing at least one fatty binder and/or at least one pulverulent compound, and including in said composition a non-aqueous dispersion of surface-stabilized polymer particles in at least one cosmetically, dermatologically, pharmaceutically or hygienically acceptable liquid fatty substance, wherein the particles are stabilized by at least one surface-stabilizing polymer.

33. A method for softening the wrinkles and/or fine lines in the skin, said method comprising applying to the skin a cosmetic, dermatological, pharmaceutical or hygiene composition containing a non-aqueous dispersion of non-film-forming surface-stabilized polymer particles in at least one cosmetically, dermatologically, hygienically or pharmaceutically acceptable non-volatile liquid fatty substance, wherein said dispersion has a solids content of at least 15% by weight and wherein the particles are stabilized by at least one surface-stabilizing polymer.

34. A method for preparing a cosmetic composition comprising the step of including in said composition at least one fatty substance and optionally at least one pulverulent compound, and a non-aqueous dispersion of surface-stabilized polymer particles in at least one liquid fatty substance, wherein the particles are stabilized by at least one surface-stabilizing polymer.

35. A cosmetic composition comprising:
at least one pulverulent compound, and
a non-aqueous dispersion of surface-stabilized polymer particles in at least one liquid fatty substance, wherein said particles are particles of at least one polymer, and wherein said polymer particles are stabilized by at least one surface-stabilizing polymer.

36. A composition according to claim 35, wherein said at least one polymer is a radical polymer, a polycondensate, or a polymer of natural origin.

37. A composition according to claim 35, wherein said at least one liquid fatty substance comprises at least one oil which is a carbon-based oil of mineral, animal, plant or synthetic origin, a hydrocarbon oil of mineral, animal, plant or synthetic origin, a fluoro oil of mineral, animal, plant or synthetic origin, or a silicone oil of mineral, animal, plant or synthetic origin.

38. A composition according to claim 35, wherein said at least one liquid fatty substance is a liquid paraffin, a liquid petrolatum, a mink oil, a turtle oil, a soya oil, a perhydrosqualene, a sweet almond oil, a calophyllum oil, a palm oil, a grapeseed oil, a sesame oil, a corn oil, a grapeseed oil, a sunflower oil, a cotton oil, a castor oil, an avocado oil, a jojoba oil, an olive oil, a cereal germ oil, an ester of lanolic acid, an ester of oleic acid, an ester of lauric acid, an ester of stearic acid, a fatty ester, a higher fatty acid, a higher fatty alcohol, a silicone oil, which is optionally phenylated or which is optionally substituted with an aliphatic group or an aromatic groups, wherein said aliphatic group or said aromatic group is optionally fluorinated, or substituted with functional groups; a polysiloxane modified with fatty acids, with fatty alcohols or with polyoxyalkylenes, a fluoro silicone, a perfluoro oil, an isoparaffin, or a volatile oil.

39. A composition according to claim 35, wherein said at least one liquid fatty substance is:
a non-aqueous liquid compound having a global solubility parameter according to the Hansen solubility space of less than 17 $(MPa)^{1/2}$, or
a monoalcohol having a global solubility parameter according to the Hansen solubility space of less than or equal to 20 $(MPa)^{1/2}$.

40. A composition according to claim 35, wherein said at least one surface-stabilizing polymer is a sequential polymer, a grafted polymer or a random polymer.

41. A composition according to claim 35, wherein said at least one fatty substance is a wax which is of plant, animal, mineral or synthetic origin or which is silicone-based, an oil which is of plant, animal, mineral or synthetic origin or which is silicone-based, a gum which is of plant, animal, mineral or synthetic origin or which is silicone-based, or a pasty fatty substance which is of plant, animal, mineral or synthetic origin or which is silicone-based.

42. A composition according to claim 35, wherein said composition is in the form of a stick or pencil; in the form of a flexible paste, with a dynamic viscosity at 25° C. of about 3–30 Pa·s; or in the form of a cupel.

43. A composition according to claim 35, wherein said composition is a skin care product or a make-up product.

44. A composition according to claim 35, wherein said composition is in the form of a body powder, a baby powder, an antiperspirant powder or a make-up product.

45. A composition according to claim 35, wherein said composition is in the form of an oily gel, an oily liquid, an oil, a paste, a stick, an aerosol, or a vesicle dispersion containing at least one lipid which is ionic or nonionic.

46. A composition according to claim 35, wherein said composition is in the form of an antisun composition, an artificial tanning composition, or a cosmetic, dermatological, hygiene or pharmaceutical composition for protection, treatment or care of the face, the neck, the hands or the body.

47. A method for preparing a cosmetic composition comprising the step of including in said composition at least one pulverulent compound, and a non-aqueous dispersion of surface-stabilized polymer particles in at least one liquid fatty substance, wherein the particles are stabilized by at least one surface-stabilizing polymer.

* * * * *